United States Patent
Nath et al.

(10) Patent No.: US 7,398,703 B2
(45) Date of Patent: Jul. 15, 2008

(54) PROCESS FOR THE ESTIMATION OF VOLATILE SUBSTANCES IN A SAMPLE

(75) Inventors: Amit Nath, Solan (IN); Surender Kumar Patyal, Solan (IN); Jatinder Kumar Dubey, Solan (IN)

(73) Assignee: Dr. Y.S. Parmar University of Horticulture & Forestry, Himachal Pradesh (IN)

( * ) Notice: Subject to any disclaimer, the term of this patent is extended or adjusted under 35 U.S.C. 154(b) by 45 days.

(21) Appl. No.: 10/524,496

(22) PCT Filed: Apr. 28, 2003

(86) PCT No.: PCT/IN03/00169

§ 371 (c)(1),
(2), (4) Date: Sep. 27, 2005

(87) PCT Pub. No.: WO2004/016657

PCT Pub. Date: Feb. 26, 2004

(65) Prior Publication Data

US 2006/0096359 A1  May 11, 2006

(30) Foreign Application Priority Data

Aug. 14, 2002  (IN)  .............................. 844/DEL/02

(51) Int. Cl.
*G01N 1/14* (2006.01)
*G01N 30/18* (2006.01)

(52) U.S. Cl. .................. 73/864.81; 73/23.35; 73/23.41; 73/864.01

(58) Field of Classification Search ..... 73/23.35–23.42, 73/863, 864.01, 864.81, 864.85; 96/101, 96/105; 422/89
See application file for complete search history.

(56) References Cited

U.S. PATENT DOCUMENTS

| 3,205,700 | A | * | 9/1965 | Lively et al. ................ 73/19.02 |
| 5,191,211 | A | * | 3/1993 | Gorman, Jr. ................ 250/282 |
| 5,266,496 | A | * | 11/1993 | Dacruz ....................... 436/157 |
| 5,363,707 | A | * | 11/1994 | Augenblick et al. ...... 73/864.84 |
| 5,545,879 | A | * | 8/1996 | Brotz .......................... 219/689 |
| 5,711,786 | A | * | 1/1998 | Hinshaw ........................ 95/82 |

(Continued)

FOREIGN PATENT DOCUMENTS

EP  464968 A2 * 1/1992

OTHER PUBLICATIONS

Overton et al., "Flavor/Fragrance Profiles of Instant Coffee and Ground Coffee by Short Path Thermal Desorption", available on the Internet at <http://www.sisweb.com/reference/applnote/ap11-a.htm>.*

(Continued)

*Primary Examiner*—Hezron E. Williams
*Assistant Examiner*—David A. Rogers
(74) *Attorney, Agent, or Firm*—The Webb Law Firm

(57) ABSTRACT

A process for the estimation of volatile substances which comprises the steps of: (i) heating distilled water in a flask to a first temperature, (ii) adding the sample to be tested into said heated water, (iii) closing the flask, (iv) maintaining the flask containing the sample at a second temperature lower than said first temperature, (v) purging with air, (vi) drawing the volatile vapours and subjecting it to analysis.

9 Claims, 1 Drawing Sheet

U.S. PATENT DOCUMENTS

| | | | | |
|---|---|---|---|---|
| 5,792,423 | A * | 8/1998 | Markelov | 422/83 |
| 6,286,375 | B1 * | 9/2001 | Ward | 73/863.12 |
| 6,395,560 | B1 * | 5/2002 | Markelov | 436/181 |
| 6,537,802 | B1 * | 3/2003 | Alocilja et al. | 435/287.5 |

OTHER PUBLICATIONS

Lindinger et al.,"Analysis of trace gases at ppb levels by proton transfer reaction mass spectrometry (PTR-MS)", Plasma Sources and Science and Technology, 1997, vol. 6, pp. 111-117.*

Wang et al., "Analysis of Trace Volatile Organics Compounds in Coffee by Headspace Concentration and Gas Chromatography-Mass Spectrometry", 1983, Chromatograpia, vol. 17, No. 8, pp. 411-417.*

Masteron, "Chemical Principles 6$^{th}$ Edition", 1985, pp. 322-328.*

Overton et al., "Flavor/Fragrance Profiles of Instant Coffee and Ground Coffee by Short Path Thermal Desorption", Dec. 23, 1999, available on the Internet at <http://www.sisweb.com/reference/applnote/ap11-a.htm>.*

* cited by examiner

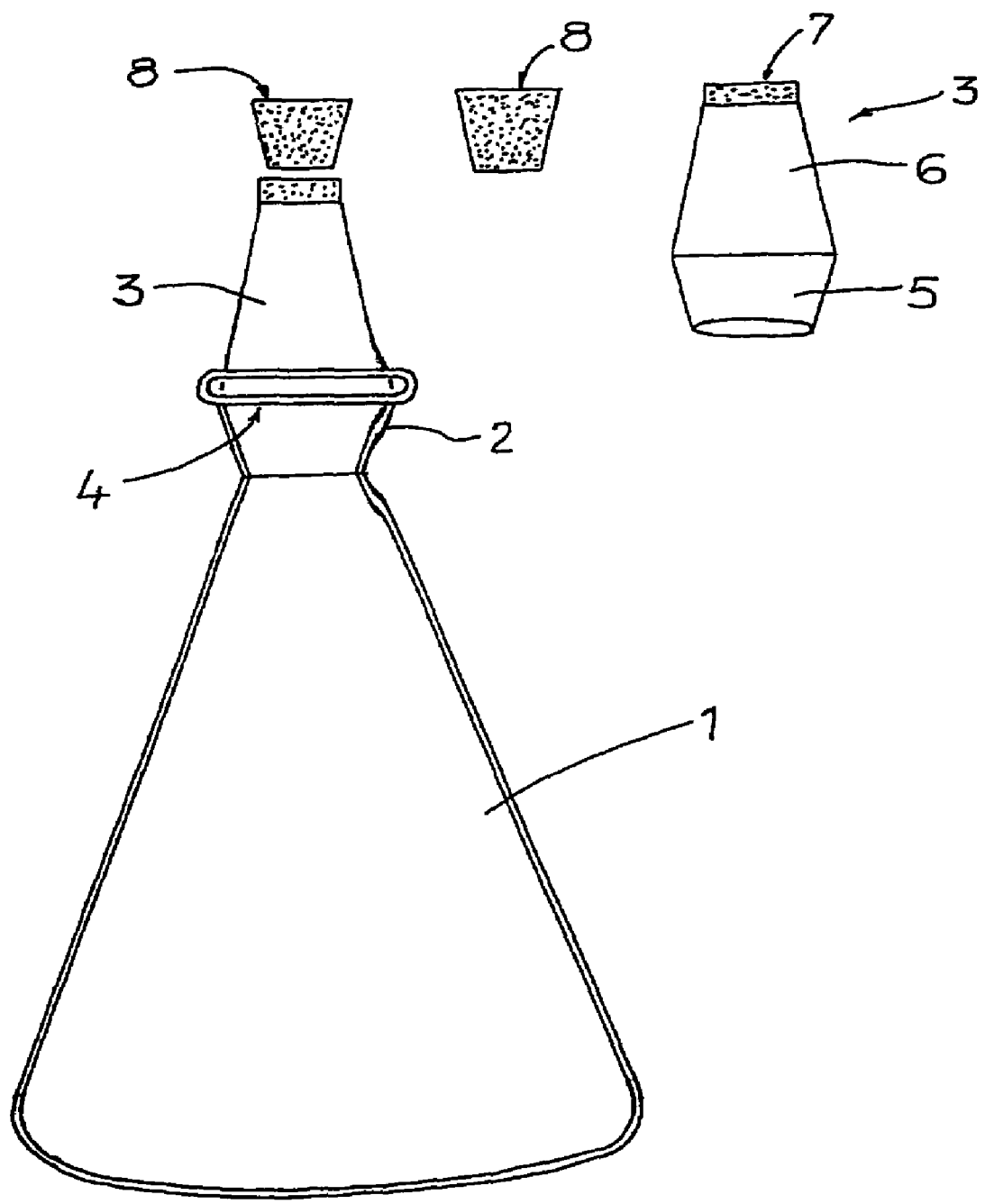

PROCESS FOR THE ESTIMATION OF VOLATILE SUBSTANCES IN A SAMPLE

FIELD OF INVENTION

This invention relates to a process for the estimation of volatile substances. Such volatile substances can, for example, be flavors and volatile pollutants in edible matter.

BACKGROUND OF THE INVENTION

There is fixed permissible limit for bacterial/microbial count in the food stuff. To keep microbial count below the limit, food material is treated with bleaching powder/chlorine water, which leads to the generation of chloroform residues. Since chloroform is a carcinogen, the Maximum Residue Limit (MRL) is fixed at 100 ppb in the food stuff.

Two known processes are known in the art for determination of chloroform residues in food stuff.

Purge and trap method in which chloroform residues from food are trapped in resin, and later eluted and estimated. Such a process requires high cost resin and ultra pure solvents in addition to costly apparatus.

Another method known in the art, is the headspace method and in which vapours are drawn from the headspace of a septurn-sealed vial containing a sample to be analysed. The vial is heated to drive out dissolved organics out of solution and into the vapour heapace (Ward; Clydie, U.S. patent application No. 301385 dated Apr. 27, 1999; U.S. Pat. No. 6,286,375).

In another method, the vial containing volatile sample is heated and agitated to enhance a transport rate of the volatile sample from material to the headspace of the vial (U.S. Pat. No. 6,146,895, Nov. 14, 2000).

For extraction Ray, et al., 1997 proposed extractor having sample chamber pressurizable either by gas or mechanical means. The sample chamber was constructed with removable liner of poly tetrafluorethylene (U.S. Pat. No. 5,607,234 Mar. 4, 1997).

Augenblick et al. 1994 describes yet another method and apparatus for collecting gases from the sample headspace of sealed container. Gas sample from the headspace to instrument was carried by carrier gas (U.S. Pat. No. 5,363,707 dated Nov. 15, 1994). Vibration is used to promote the formation of sample gas.

Main drawbacks of these aforesaid processes:
1. Heating of vessel containing sample causes development of high pressure within the vessel and cause explosion and injuries.
2. Additional carrier gas is required, which increase the cost of analysis.
3. Additional instruments such as vibrator are required, which increases the cost of analysis.
4. Small size vials are used, which are unable to accommodate large size samples.
5. Bags are used which can break a high temperature and pressure.
7. High capital cost.
8. Danger of breakdown of labile compounds at prolonged high temperature and therefore lower estimation.

OBJECT OF THE INVENTION

An object of this invention is to propose a process for the estimation of volatile substances.

Another object of this invention is to propose a process for the estimation of volatile substances, which obviates the disadvantages associated with those of the prior art.

Yet another object of this invention is to propose a process for the estimation of volatile substances and wherein chloroform residues are released from the sample into a headspace under partial vacuum or at low pressure whereby reducing risk of leakage of volatile substances.

Still another object of this invention is to propose a process for the estimation of volatile substances and wherein no additional carrier gas is required.

A further object of this invention is to propose a process for the estimation of volatile substances and wherein prolonged high temperature is not required.

A still further object of this invention is to propose a process for the estimation of volatile substances, which involves low cost of apparatus.

DESCRIPTION WITH REFERENCE TO DRAWINGS

Further objects and advantages of this invention will be more apparent from the ensuing description when read in conjunction with the accompanying drawing, which illustrates an exploded view of the flask of the present invention.

The flask 1 has a neck 2. A stopper 3 is adapted to close the mouth 4 of flask 1. Stopper 3 has a lower section 5, which is a conical member and an upper frusto conical section 6. Mouth 7 is adapted to be closed by a closure 8.

DESCRIPTION OF INVENTION

According to this invention there is provided a process for the estimation of volatile substances which comprises in the steps of:
i) heating distilled water in a flask to a first temperature,
ii) adding the sample to be tested into said heated water,
iii) closing the flask,
iv) maintaining the flash containing he sample at a second temperature lower than said first temperature,
v) purging the flash with air,
vi) drawing the volatile vapours and subjecting it to analysis.

Further according to this invention there is provided an apparatus is for the estimation of volatile substances cans comprising a flask having a stopper adapted to fit and close the mouth of said flask, a closure member for closing the mouth of said stopper.

In accordance with this invention, distilled water is heated to a first temperature under atmospheric conditions. Such a first temperature can, for example, be the boiling temperature of water, and particularly when an estimator of chloroform and other similar compounds is required. However, for more volatile compounds present in edibles, residues can be estimated by raising water temperature lower than the boiling temperature. Such a temperature depends upon the nature of the volatile compound.

Thereafter, the flask is removed from the heat source and the sample to be analyzed is introduced into said flask and then maintained at a second temperature lower than said first temperature. However, after introducing the sample into said flask, the flask is closed. As the flask is in a closed status and he temperature reduced from a first to a second temperature, a vacuum or low pressure is created within said flask. By way of example and without implying any limitation thereto, the first temperature is the boiling temperature and the second temperature is approximately 40° C. to 45° C. in the instance of chloroform and similar compounds. However, in the instance of compounds having higher vapour pressure, the second temperature can be lower that 40° C. to 45° C.

The flask is maintained at the second temperature for approximately 45 minutes. Thereafter, the vacuum is broken by purging air into the flask Turbulence is caused within said vessel so as to disperse the volatile substances into the head space with the closed flask. A sample is removed from the headspace and analyzed.

Preferably the sample is wrapped in a foil and introduces into the flask.

Several distinct advantages ensue by the present advantages. As the sample is added to boiling water, there is flask heating and not sustained heating of the sample, and whereby decomposition of the sample is prevented and formation of undesirable compounds avoided. It has been found that water can also be heated to a temperature lower than the boiling temperature. However, the second temperature would then need to be adjusted. Primarily, the first and second temperature is to provide a reduced pressure or vacuum within the closed vessel, as a volatilization is more effective at a reduced pressure or vacuum. In the known art, volatilization was less effective as it was carried out at high pressure.

Thus, the present invention is based on volatile compounds being released from the plant matrix under reduced pressure. Released volatile compounds accumulate in the headspace from where they can be collected and analysed. Further more it has been found that equilibration of closed container, containing sample in vacuum, at a constant temperature was important for the reproducibility of results.

Thus according to one aspect of the present invention there is closed container containing sample/volatile material and water. Sample is added prior to closure of the container.

Examples of closed containers which may be useful in accordance with invention include glass flask (250 ml) with B-24 neck this flask is attached with 7 cm stopper having B-24 joint at one end and 1.5 cm diameter dole at the top closed by a 2 cm silicon cork.

The volatile substance may in general comprise of flavours present in food, beverages and other additives. However, other contaminants like halogens can be estimated too.

Boiling of water prior to adding sample expel the air inside the flask and when temperature of flask is lowered vacuum is created which causes the release of volatile substances from the plant matrix. Thus the processes involving introduction of plant matrix/sample into the boiled water and equilibrating at a constant temperature followed by introduction of air, is the point of completion of the treatment.

Working Examples:

Example-I

Weigh 1 g crop material into a aluminimum foil and fold loosely in a packet form so that crop material could easily come in contact with the water, after its insertion into the flask. First take thirty milliliter distilled water in 250 ml flask, boil then replace flask from the heat source, push in the packet containing the material and immediately encap with stopper (stopper plugged with silicon cork). Swirl the flask until material from de aluminum foil come in the contact with the warm water. Equilibrate the flask 40° C. for one hour in the incubator. At the end, insert needle of 10 ml syringe through the silicon cork and introduce air into it for 30 seconds. Replace the plunger, move plunger up and down three times. Then suck 10 ml vapours from the flask into the syringe and then take out the syringe. Out of 10 ml vapours expel 9 ml and inject remaining vapours into gas chromatograph fitted with ECD and capillary column for qualitative and quantitative estimation.

Example-II

Step I Take 0.1 ml chloroform (ca. 140 mg) in 10 ml methanol which will five strength of ca. 14000 pts per million (ppm).

Step II Take 1 ml of step I solution in 100 ml of water whose strength will be equivalent to ca. 14000 part per billion (ppb).

| | Step III- | |
| --- | --- | --- |
| Desired strength (ppb) 1 | Volume (ml) of step II (14000 ng/ml) stock solution required to make total 10 ml solution in water. 2 | Strength of working solution required for fortification. (ppb) 3 |
| 25 | 0.18 | 250 |
| 50 | 0.36 | 500 |
| 100 | 0.71 | 1000 |
| 150 | 1.07 | 1500 |
| 200 | 1.43 | 2000 |

Step IV Take 0.1 ml working solution as per Step III column 3 of the above table and fill it in the disposable dispensable dispenser's tip.

Step V Insert the filled tip into the flask after removing the flask (containing water) from the heat source.

Step VI Immediately encap the flask with the glass stopper containing silicon cork at top. Equilibrate the flask at 40° C. for one hour in the incubator. At the end, insert needle of 10 ml syringe through the silicon cork and introduce air into it for 30 seconds. Replace the plunger, move plunger up and down three times. Then suck 10 ml vapours from the flask into the syringe and then take out the syringe. Out of 10 ml vapours expel 9 ml and inject remaining vapours into gas chromatograph fitted with capillary column (0.35 μand 35 m long) for qualitative and quantitative estimation. Keep oven, injection port an detector temperature at 70° C., 100° C., and 300° C., respectively. Under these conditions minimum detection limit for chloroform is 5 ppb.

We claim:

1. A process for the estimation of volatile substances, comprising the steps of:
   i) heating distilled water in a flask to a first temperature,
   ii) adding a sample to be tested into said heated water,
   iii) closing the flask via a stopper having a cork at one end,
   iv) maintaining the flask containing the sample at a second temperature lower than said first temperature,
   v) purging the flask with air by inserting a syringe needle through the cork and inserting air into the flask,
   vi) moving a plunger of the syringe up and down a plurality of times in order to cause turbulence in the flask, and
   vii) drawing up the volatile substances and subjecting it to analysis.

2. The process as claimed in claim 1, wherein volatilization of the volatile substances is carried out at low pressure.

3. The process as claimed in claim 1, wherein volatilization of the volatile substances is carried out in vacuum.

4. The process as claimed in claim 1, wherein the first temperature is the boiling temperature of water.

5. The process as claimed in claim 1, wherein the heating of water is carried out at atmospheric pressure.

6. The process as claimed in claim 1, further comprising equilibrating the flask at the lower temperature for about one hour.

7. The process as claimed in claim 1, wherein the syringe sucks up a volume of the volatile substances.

8. The process as claimed in claim 1, wherein about 10 ml. of headspace sample is sucked up.

9. The process as claimed in claim 8, further comprising expelling most of the volatile substances from the syringe and injecting the remaining volatile substances into a chromatograph fitted with an electron capture detector and capillary column for quantitative estimation.

* * * * *